(12) United States Patent
Lee et al.

(10) Patent No.: US 6,251,782 B1
(45) Date of Patent: Jun. 26, 2001

(54) SPECIMEN PREPARATION BY FOCUSED ION BEAM TECHNIQUE

(75) Inventors: Angela Y.C. Lee, Hsinchu; Ting Chou, Taipei, both of (TW)

(73) Assignee: Vanguard International Semiconductor Corporation, HsinChu (TW)

( * ) Notice: Subject to any disclaimer, the term of this patent is extended or adjusted under 35 U.S.C. 154(b) by 0 days.

(21) Appl. No.: 09/361,027

(22) Filed: Jul. 23, 1999

(51) Int. Cl.[7] .................................................. H01L 21/302

(52) U.S. Cl. .............................. 438/689; 438/46; 438/47; 216/33

(58) Field of Search ................................. 438/10, 14, 18, 438/52, 53, 45, 46, 522, 734, 676, 689; 257/25, 627, 231, 399, 797, 706

(56) References Cited

U.S. PATENT DOCUMENTS 6,042,736 * 3/2000 Chung ..................................... 216/33

* cited by examiner

*Primary Examiner*—David Nelms
*Assistant Examiner*—Dung A Le
(74) *Attorney, Agent, or Firm*—Tung & Associates

(57) ABSTRACT

A method for preparing small area parallel lapping specimens by a focused ion beam technique is disclosed in which a multiple-staged ion beam milling process is used to prepare a specimen for microscopic examination. The method may be carried out by first providing a high current ion beam for removal of a top surface of a specimen exposing a surface that immediately covers the characteristic feature to be examined to define a small window area that contains the characteristic feature. The present invention novel method may further be combined with a wet etching step after the ion beam milling process is completed. In the wet etching step, a three dimensional surface containing the characteristic feature to be examined is revealed which can then be observed under a scanning electron microscope.

15 Claims, 1 Drawing Sheet

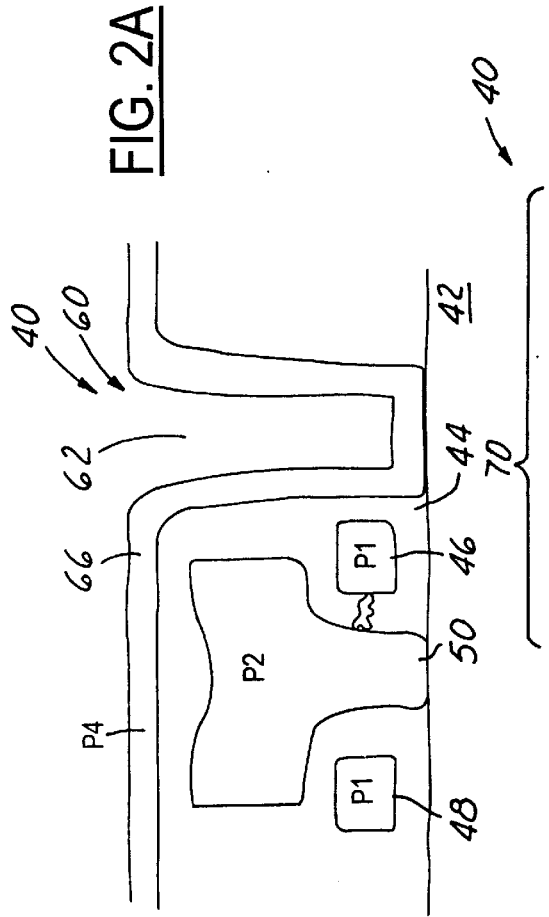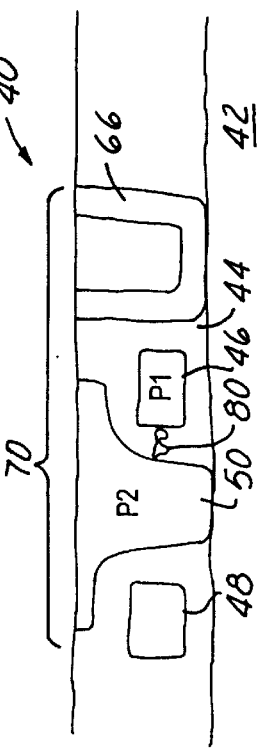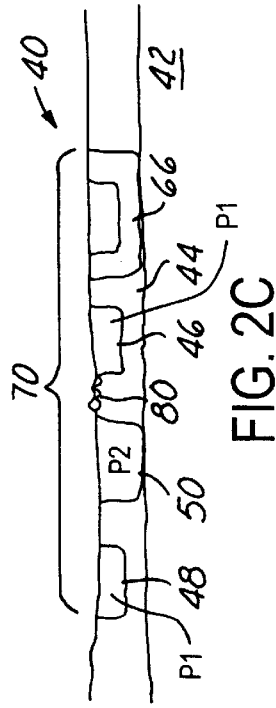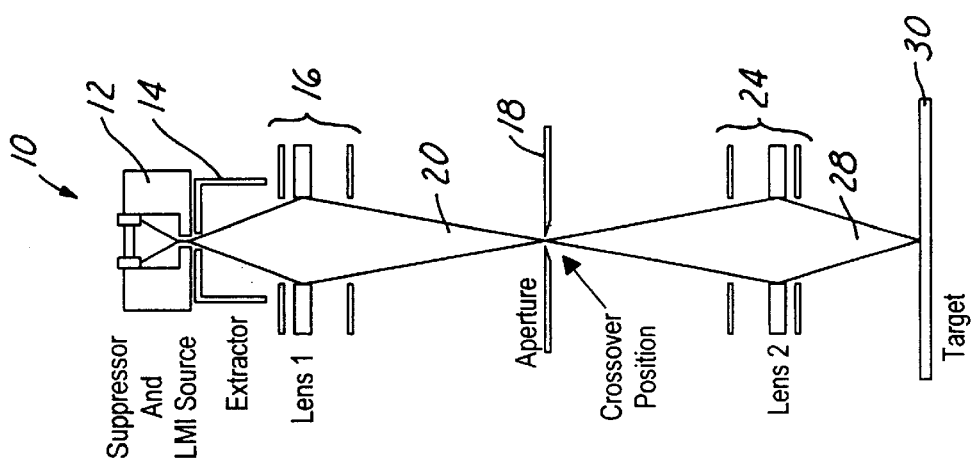

SPECIMEN PREPARATION BY FOCUSED ION BEAM TECHNIQUE

FIELD OF THE INVENTION

The present invention generally relates to a method for preparing small area parallel lapping specimens by a focused ion beam technique and more particularly, relates to a method for preparing small area parallel lapping specimens by a focused ion beam technique in which a high beam current is first used to prepare a large surface for setting up boundaries for a window area that contains a structural feature to be examined, and then followed by a low beam current for removing layers in the window area to expose the structural feature.

BACKGROUND OF THE INVENTION

In the failure analysis of electronic structures, a specimen of the electronic structure that contains a defect is frequently prepared for microscopic examination. For instance, a specimen of an electronic structure such as a semiconductor wafer is frequently analyzed in a scanning electron microscope (SEM) or a transmission electron microscope (TEM) to study a specific characteristic feature in the semiconductor device. The characteristic feature may include a circuit fabricated or a defect formed during the fabrication process. SEM is one of the most useful equipment for analyzing the microscopic structure of semiconductor devices which provides the benefits of a three-dimensional image for analyzing a structure and a simple specimen preparation method.

In preparing specimens of a semiconductor wafer for electron microscopic examination, various polishing and milling processes are used to section the structure until a specific characteristic feature is exposed. As device dimensions are continuously reduced to the sub-half micron level, the techniques for preparing specimens for study in an electron microscope have become more important. The conventional methods for studying structures by an optical microscope cannot be used to study features in a modem electronic structure due to its low resolution.

Generally, when a specimen is prepared for an electronic microscopic study of a characteristic features, various mechanical polishing and grinding techniques are used to first bring the dimension of a specimen down to a size just before the characteristic feature is reviewed. A final sample preparation step is then accomplished by a method such as ion milling. The ion milling method is frequently conducted by a focused ion beam (FIB) technique.

In a FIB technique, focused ion beams are used to either locally deposit or remove materials. A cluster of ionized beam consists of an aggregate of from 100 to 2,000 atoms is aimed at a sample surface. When the cluster impacts the surface of an electronic structure, the cluster disintegrates into atoms which are then scattered over the surface to remove a surface layer of the material. Typical ion beams have a focused spot size of smaller than 100 nm when produced by a high intensity source. Sources of such high intensity ions can be either liquid metal ion sources or gas field ion sources. Both of these sources have a needle type form that relies on field ionization or evaporation to produce the ion beam. After the ion beam is produced, it is deflected in a vacuum and directed to a desired surface area. The focused ion beams can be suitably used in semiconductor processing industry as a cutting or attaching tool to perform a circuit repair, a mask repair or a micro-machining process.

A cutting or milling process is normally performed by locally sputtering a surface with a focused ion beam. In an ion beam milling process, where a material is selectively etched by a beam of ions such as $Ga^+$ focused to a submicron diameter, the technique is often referred to as focused ion beam etching or milling. FIB milling is a very useful technique for restructuring a pattern on a mask or an integrated circuit, and for diagnostic cross-sectioning of micro structures. In a typical FIB etching process, a beam of ions such as $Ga^+$ is incident onto a surface to be etched and the beam can be deflected to produce a desirable pattern. In the etch chamber, a gas such as $Cl_2$ can be introduced to fill the chamber to a pressure of about 30 m Torr, while the vacuum outside the chamber where the FIB is generated is normally maintained at approximately $10^{-7}$ Torr. The focused ion beam can be used to bombard a specimen surface at a very low angle, i.e., as low as 0~5°, such that a cavity can be formed on the surface of an electronic structure to reveal a characteristic feature of the structure for electron microscopic examination.

In the preparation of a sample surface by the FIB technique, extreme care must be exercised to reveal the characteristic feature without damaging it such that an accurate examination can be made. A FIB technique is most suitable for preparing such a microscopic sample when a cavity is cut into the sample since the technique can be used to simultaneously cutting and observing the sample surface at the same time. Furthermore, the sample specimen in a FIB machine can be tilted to any desirable angle less than 50° such that a cavity of a desirable shape can be formed in the surface. The FIB technique utilizes a primary beam of ions for removing a layer of material at a high current, and then observing the surface that was newly formed at a low current. The observation of the surface is made by detecting the secondary electrons emitted from the sample surface when the surface is bombarded by the ions. A detector is used to receive the secondary electronics emitted from the surface to form an image. The FIB method, even though cannot produce an image at a high resolution such as that obtainable in a SEM/TEM technique, can be used to sufficiently identify a newly formed cross-sectional surface which may contain the characteristic feature to be examined. The capability of the FIB technique for making observations down to a resolution of 5~10 nm enables the cutting of a precise plane in an electronic structure such that it may be later examined by a SEM or TEM technique at a higher resolution than that available from FIB.

Parallel lapping is a technique for preparing a planar specimen which shows the plane, instead of a cross-section, of an electronic structure. Conventionally, a polishing or grinding technique is used to gradually removing layers from an outer surface toward the interior of the specimen until the specific layer containing a characteristic structure is reached. The structure is then etched in a wet etchant such that it may be observed in SEM for studying the characteristic feature or defect and its reason for being defective. Several problems are encountered when the parallel lapping technique is used to prepare a planar specimen. First, when the parallel lapping technique is used to remove layers in a parallel plane of the specimen, the peripheral area of the specimen is normally removed at a higher speed while the center of the specimen is removed at a lower speed. As a result, a non-planar surface is normally obtained by the parallel lapping technique. Secondly, an optical microscope is normally used to examine the surface layer obtained after the parallel lapping process. However, many characteristic features to be observed, i.e., a failed bit in a memory device, cannot be readily observed under an optical microscope, since the maximum magnification ratio obtainable in an optical microscope is only about 2000x. It is therefore difficult to identify a minute structural feature under the optical microscope and to determine whether a suitable layer has been removed and revealed in the specimen.

Attempts have been made in using SEM to determine the polishing layers, or whether a characteristic feature has been revealed by the specific layer. The SEM technique requires an elaborate specimen preparation technique and the attainment of a high vacuum in the specimen chamber which is time consuming and requires a high level of skill.

The FIB technique is therefore a suitable method for sample preparation for examination by SEM or TEM. A typical focused ion beam arrangement is shown in FIG. 1. The FIB apparatus 10 is constructed of a suppressor and a liquid metal ion source 12 wherein the liquid metal ion may be gallium, an ion extractor 14, a three-element asymmetric lens 16, and an electrostatic aperture adjustment 18. The ion beam 20, after crossing over at the aperture 18, is treated by a second three-element asymmetric lens 24 before the ion beam 28 is impinged on a target 30. The operating modes include a beam control pattern which intermittently blanks the ion beam and allows the ion charge to dissipate, thus reducing electrostatic discharge damage. The ion beam 20 is advantageously focused with a column that includes the three-element asymmetric lens assembly 16 and 24. The ion beam 28 produced by the apparatus 10 has superior position stability and high current density. The ion beam further has a fine probe diameter and beam placement accuracy capable of high performance versatility of a full digital beam scanning process.

It is therefore an object of the present invention to provide a method for preparing a small area parallel lapping specimen by a focused ion beam technique which does not have the drawbacks or shortcomings of the conventional methods.

It is another object of the present invention to provide a method for preparing small area parallel lapping specimens by a focused ion beam technique by utilizing a multi-stage ion beam etching process.

It is a further object of the present invention to provide a method for preparing small area parallel lapping specimens by a focused ion beam technique in which an ion beam of a high beam current is first used to remove a layer of the specimen for exposing a surface immediately adjacent to a characteristic feature to be examined.

It is another further object of the present invention to provide a method for preparing small area parallel lapping specimens by a focused ion beam technique in which a high beam current is first used to remove a surface layer of the specimen and then followed by a low beam current for defining a small window area which contains a characteristic feature to be examined.

It is still another object of the present invention to provide a method for preparing small area parallel lapping specimens by a focused ion beam technique in which a high beam current is first used to remove a surface area and define a small window area, followed by a low beam current for removing a second surface area in the small window section to expose a characteristic feature.

It is yet another object of the present invention to provide a method for preparing small area parallel lapping specimens by a focused ion beam technique in which a high beam current of at least 400 pA and a low beam current of less than 200 pA are utilized in different stages of the specimen preparation process.

It is still another further object of the present invention to provide a method for preparing small area parallel lapping specimens by a focused ion beam technique in which a wet etching process is conducted after the ion beam milling process to prepare a three dimensional structure of the characteristic feature for microscopic examination.

It is yet another further object of the present invention to provide a method for preparing small area parallel lapping specimens by a focused ion beam technique in which a high beam current and a low beam current are both used with the low beam current not more than one half of the high beam current.

SUMMARY OF THE INVENTION

In accordance with the present invention, a method for preparing a small area parallel lapping specimen by a focused ion beam technique wherein multiple stages of milling by both high beam current and low beam current of the focused ion beam are utilized to prepare samples in a small window area between about 0.5 $\mu$m×0.5 $\mu$m and about 20 $\mu$m×20 $\mu$m is disclosed.

In a preferred embodiment, a method for preparing small area parallel lapping specimens by a focused ion beam technique can be carried out by the operating steps of first providing an integrated circuit that has multiple layers deposited on a substrate and a characteristic feature to be examined, removing layers in the multiple layers including a bottom-most metal conductor layer exposing a first surface, directing a FIB at a first beam current on the first surface removing a first layer of material and exposing a second surface immediately adjacent to the characteristic feature to be examined, directing a FIB at a second beam current lower than the first beam current on the second surface defining a boundary for a window area containing the characteristic feature by removing a second layer of material, exposing the characteristic feature.

The method may further include the step of etching a surface containing the characteristic feature with a wet etchant such that a three-dimensional structure is obtained. The step of removing layers in the multiple layers including a bottom-most metal conductor layer may be carried out by a mechanical polishing step. The first beam current may be at least 400 pA. The second beam current is not more than 200 pA. The small area parallel lapping specimens are prepared by a two-stage high beam current/low beam current process. The method may further include the step of examining the three-dimensional sample surface by scanning electron microscopy. The second beam current is at least 5 pA smaller than the first beam current, and preferably at least 50 pA smaller than the first beam current. The characteristic feature observed may be a failed bit in a memory device.

In another preferred embodiment, a method for preparing small area parallel lapping specimens by a focused ion beam technique can be executed by the operating steps of first providing an integrated circuit that has multiple layers deposited on a substrate and a characteristic feature to be examined, removing layers in the multiple layers including a bottom-most metal conductive layer to expose a first surface, directing a FIB of a first beam current on the first surface removing a first layer of material and exposing a second surface immediately adjacent to the characteristic feature to be examined, directing a FIB of a second beam current lower than the first beam current on the second surface defining a boundary for a window area containing the characteristic feature by removing a second layer of material, directing a FIB current substantially the same as the first beam current on the window for removing a third layer of material exposing the characteristic feature, etching a surface containing the characteristic feature with a wet etchant such that a three dimensional structure is reviewed.

The step of removing layers including a bottom-most metal conductor layer may be carried out by a mechanical polishing method. The first beam current is at least 400 pA while the second beam current is not more than 200 pA. The second beam current is at least 5 pA smaller than the first beam current, and preferably at least 50 pA smaller than the first beam current. The characteristic feature observed may be a failed bit in a semiconductor device.

BRIEF DESCRIPTION OF THE DRAWINGS

These and other objects, features and advantages of the present invention will become apparent from the following detailed description and the appended drawings in which:

FIG. 1 is a schematic illustrating a conventional focused ion beam apparatus effective in ion beam milling.

FIG. 2A is an enlarged, cross-sectional view of a present invention semiconductor structure that contains a characteristic feature to be examined between two polysilicon conducting layers.

FIG. 2B is an enlarged, cross-sectional view of the present invention semiconductor structure of FIG. 2A having a top layer of the structure removed.

FIG. 2C is an enlarged, cross-sectional view of the present invention semiconductor structure of FIG. 2B having another surface layer removed to review the characteristic feature to be examined.

DETAILED DESCRIPTION OF THE PREFERRED EMBODIMENT

The present invention discloses a method for preparing small area parallel lapping specimens by a focused ion beam technique in which multiple stages of ion beam milling process is utilized including a high beam current to first remove a top layer of material and expose a surface immediately adjacent to a characteristic feature to be examined, then a low beam current for defining a boundary for a small window area that contains the characteristic feature to be examined. The present invention novel method may further include the step of wet etching the specimen by a wet etchant such that a three-dimensional structure can be obtained for observation under a scanning electron microscope.

The present invention novel method greatly improves the conventional method of parallel lapping by a mechanical means such as by hand polishing with sand paper which is extremely difficult to control the exact layers removed in order to reveal the characteristic feature to be examined. When a hand polishing method is used, the polishing speed and the pressure placed on the specimen are very difficult to control. As a result, a high failure rate is normally encountered in preparing specimens by hand polishing. Moreover, the surface of the specimen must be constantly examined under an optical microscope to determine whether sufficient layers of the material have been removed.

The present invention novel method of small area parallel lapping specimen preparation by a focused ion beam technique can be carried out at a success rate of almost 100%. Furthermore, by using a focused ion beam apparatus at the various beam currents taught by the present invention, the complete specimen preparation process can be finished in less than one hour. This is compared to a conventional method which normally requires at least half a day or a whole day.

The present invention novel method may be explained below in conjunction with an examination of FIGS. 2A–2C wherein P1 denotes polysilicon layer 1, P2 denotes polysilicon layer 2 and P4 denotes polysilicon layer 4. First, a semiconductor structure 40 which is essentially a memory device is provided. The semiconductor structure 40 is built on a silicon wafer 42 onto which polysilicon floating gates 46, 48 for active regions (not shown) are formed. A second polysilicon gate 50 is then patterned in an oxide insulating layer 44 and formed. The polysilicon 50 is the second polysilicon layer and can be expressed as a P2 layer. To complete the memory device, a control node of capacitor 60 is then formed by first forming a contact node opening 62 and then depositing a polysilicon layer 66 (the P4 layer).

In subsequent testing of the memory device 40, malfunction is discovered and thus identification of a failed bit in the device becomes necessary. In carrying out the present invention novel process, all the metal layers (not shown) above the P4 layer are first removed, for instance, by a mechanical polishing process.

The semiconductor structure 40, as shown in FIG. 2A, is then placed in a focused ion beam chamber and etched by a first (high) current density of approximately 672 pA in the vicinity of the failed bit. It should be noted that the present invention novel method is more suited for preparing a planar surface instead of a cross-sectional surface for examination. As the FIB process proceeds at 672 pA, the ion beams uniformly etch away the surface layer including the P4 layer. The progress of the material removal can be seen in a video monitor which indicates the layers that are removed in real time. The capability of the FIB apparatus of looking at a specimen preparation in real time is a great benefit which further facilitates a proper sample preparation procedure.

The high current, i.e., 672 pA, ion beam etching process continues until the P4 layer 66 appears in the video monitor. This is achieved by an actual observation of the P4 layer and the counting by CPD to the position of the failed bit, i.e., at between the floating gate 46 and the polysilcon gate 50.

The FIB apparatus is then adjusted to decrease the beam current to a low powered ion beam. For instance, at a power of about 99 pA, or in a range between about 5 pA and about 200 pA. The low beam current is used to define a small window area over the failed bit, or immediately adjacent to the failed bit, in an area between about 0.5 $\mu$m×0.5 $\mu$m and about 20 $\mu$m×20 $\mu$m. When the window area is located, the FIB makes four deep marks surrounding the failed bit to identify the area. The deep marking may reach the silicon substrate for a clear identification of the window area. This is shown in FIG. 2B as window area 70.

After the window area 70 of approximately between about 0.5 $\mu$m×0.5 $\mu$m and about 20 $\mu$m×20 $\mu$m is identified and marked by the FIB, the beam current of the FIB is again increased to approximately 672 pA or a current higher than 400 pA, to scan the surface within the window 70 marked by the four identification marks (not shown) to rapidly removing material layer for locating the failed bit. The process can be inspected in real time on a video scanner which shows the various layers exposed as the etching process proceeds. When the proper layer is identified, as shown in FIG. 2C, to expose the characteristic feature 80, the ion beam milling process is stopped. The present invention novel method is therefore completed by revealing the characteristic feature 80 in the window area 70. It was discovered that with proper sample preparation, the present invention method can be advantageously carried out in approximately one hour.

In another embodiment of the present invention novel method, a wet etching step can be used following the FIB preparation process. A suitable wet etchant can be used to etch away the insulating layer, i.e., the oxide layer, such that the failed bit of the polysilicon gate and floating gate can be shown. A three-dimensional surface can then be observed under a scanning electron microscope at a significantly higher magnification ratio than that achievable by the FIB apparatus or by the optical microscope.

The present invention novel method has therefore been amply demonstrated in the above descriptions and in the appended drawings of FIGS. 2A~2C. It should be noted that while the locating of a failed bit in a memory device is used as an illustration of the present invention method, the method is in no way limited to such application. The present invention novel process is carried out by utilizing a multiple stage milling method in which a high current ion beam is first used to remove a large surface layer until a characteristic feature is almost exposed, a significantly lower current ion beam is then used to define a small window area followed by a high beam current milling process within the small window area such that material layers can be rapidly removed to reveal the characteristic feature to be examined. The present invention novel method may further be combined with a wet etching step after the completion of the FIB process. The wet etching enables a three-dimensional surface to be maintained which can then be easily examined under a scanning electron microscope.

While the present invention has been described in an illustrative manner, it should be understood that the terminology used is intended to be in a nature of words of description rather than of limitation.

Furthermore, while the present invention has been described in terms of a preferred and several alternate embodiments, it is to be appreciated that those skilled in the art will readily apply these teachings to other possible variations of the inventions.

The embodiment of the invention in which an exclusive property or privilege is claimed are defined as follows:

1. A method for preparing small area parallel lapping specimens by a focused ion beam (FIB) technique comprising the steps of:
    providing an integrated circuit device having multiple layers deposited on a substrate and a characteristic feature to be examined,
    removing layers in said multiple layers including a bottom-most metal conductor layer exposing a first surface,
    directing a FIB at a first beam current on said first surface removing a first layer of material and exposing a second surface immediately adjacent to said characteristic feature to be examined,
    directing a FIB at a second beam current lower than said first beam current on said second surface defining a boundary for a window area containing said characteristic feature by removing a second layer of material, and
    etching material surrounding the defect and exposing said characteristic feature.

2. A method according to claim 1 further comprising the step of, after said characteristic feature is exposed, etching a surface containing the characteristic feature with a wet etchant such that a three-dimensional structure is obtained.

3. A method according to claim 1, wherein said step of removing layers in said multiple layers is carried out by a mechanical polishing means.

4. A method according to claim 1, wherein said first beam current is at least 400 pA.

5. A method according to claim 1, wherein said second beam current is not more than 200 pA.

6. A method according to claim 1, wherein said small area parallel lapping specimens are prepared by a two-stage high beam current/low beam current process.

7. A method according to claim 2 further comprising the step of examining said three-dimensional sample surface by scanning electron microscopy.

8. A method according to claim 1, wherein said second beam current is at least 5 pA smaller than said first beam current.

9. A method according to claim 1, wherein said second beam current is preferably at least 50 pA smaller than said first beam current.

10. A method according to claim 1, wherein said characteristic feature observed is a failed bit in a memory device.

11. A method according to claim 10, wherein said first beam current is at least 400 pA while said second beam current is not more than 200 pA.

12. A method for preparing small area parallel lapping specimens by a focused ion beam (FIB) technique comprising the steps of:
    providing an integrated circuit device having multiple layers deposited on a substrate and a characteristic feature to be examined,
    removing layers in said multiple layers including a bottom-most metal conductor layer exposing a first surface,
    directing a FIB at a first beam current on said first surface removing a first layer of material and exposing a second surface immediately adjacent to said characteristic feature to be examined,
    directing a FIB at a second beam current lower than the first beam current on said second surface defining a boundary for a window area containing said characteristic feature by removing a second layer of material, and
    etching a surface containing said characteristic feature with a wet etchant such that a three dimensional structure is reviewed.

13. A method according to claim 12, wherein said step of removing layers in said multiple layers including a bottom-most metal conductor layer is carried out by a mechanical polishing means.

14. A method according to claim 12, wherein said second beam current is at least 5 pA smaller than said first beam current.

15. A method according to claim 12, wherein said characteristic feature observed is a failed bit in a memory device.

* * * * *